United States Patent [19]
Ely et al.

[11] Patent Number: 5,837,848
[45] Date of Patent: Nov. 17, 1998

[54] ROOT-SPECIFIC PROMOTER

[75] Inventors: Susan Ely, Groton, N.Y.; Ian Jeffrey Evans, Reading; Wolfgang Walter Schuch, Heathlake Park, both of England

[73] Assignee: Zeneca Limited, London, England

[21] Appl. No.: 288,630

[22] Filed: Aug. 10, 1994

Related U.S. Application Data

[63] Continuation-in-part of Ser. No. 111,590, Aug. 25, 1993, abandoned, which is a continuation of Ser. No. 669,433, Mar. 15, 1991, abandoned.

[30] Foreign Application Priority Data

Mar. 16, 1990 [GB] United Kingdom ................... 9006017

[51] Int. Cl.$^6$ ........................ C12N 15/29; C12N 15/64; C12N 15/82; C12N 15/33
[52] U.S. Cl. .................. 536/24.1; 536/23.71; 536/23.6; 435/172.3; 435/240.4; 435/320.1; 800/205; 800/DIG. 56
[58] Field of Search ........................ 429/405; 435/172.1, 435/172.3, 240.4, 320.1; 536/23.2, 23.6, 24.1, 23.71; 800/205, DIG. 56; 935/6, 22, 23, 52

[56] References Cited

U.S. PATENT DOCUMENTS 4,806,669  2/1989  Puskaric ................................ 800/200

FOREIGN PATENT DOCUMENTS 388186  9/1990  European Pat. Off. .

OTHER PUBLICATIONS

Benfey, et al: "The Cauliflower Mosaic Virus 35S Promoter: Combinatorial Regulation of Transcription in Plants", Science, vol. 250: pp. 959–966.

Potrykus: "Gene Transfer to Cereals: An Assessment", Bio/Technology, 8: pp. 535–542.

Koster–Topfer, et al: "A Class II patatin promoter is under developmental control in both transgenic potato and tobacco plants", Moi Gen Genet (1989) 219: pp. 390–396.

Barton, et al: "Bacillus thruingiensis δ–Endotoxin Expresses in Transgenic Nicotiana tabacum Provides Resistance to Lepidopteran Insects", Plant Physiol.(1987)85, pp. 1102–1109.

Montoliu, et al: A tandem of α–tubulin genes preferentially expressed in radicular tissues from Zea mays Plant Molecular Biology 14: 1–15, 1989.

Hillel et al: "An Octipine Synthase Enhancer Element Directs Tissue–Specific Expression and Binds ASF–1, a Factor from Tobacco Nuclear Extracts", The Plant Cell, vol. 1,977–1984, Oct. 1989–American Society of Plant Physiologists.

Gordon–Kamm, et al: "Transformation of Maize Cells and Regeneration of Fertile Transgenic Plants", The Plant Cell. vol. 2, 603–618, Jul. 1990 American Society of Plant Physiologists.

John et al: "Isolation and Characterization of Root–Preffer-ential CDNA Clones from Zea mays", Abstracts, Journal of Cellular Biochemistry, Supplement 15A, 1991, Jan. 10 –24, 1991, p. 133.

Baynton et al: Isolation of DNA sequences determining organ enchanced expression of genes in maize [P5.03] Journal of Experimental Botany, abstracts, vol 41, May 1990.

Ludwig, et al: "A Regulatory Gene as a Novel Visible Marker for Maize Transformation" Jan. 1990, Science, vol 24, pp. 449 –450.

Kawamura et al: "Phosphoenolpyruvate Carboxylase Prevalent in Maize Roots: Isolation of a cDNA Clone and Its Use for Analyses of the Gene and Gene Expression", J. Biochem, vol. 107, No. 1, 1990 –pp. 165–168.

Kim et al. Plant Molecular Biology. 24:105–117, Jan. 1994.

*Primary Examiner*—David T. Fox
*Assistant Examiner*—Thomas Haas
*Attorney, Agent, or Firm*—Cushman Darby & Cushman Intellectual Property Group of Pillsbury Madison & Sutro LLP

[57] ABSTRACT

A DNA which has the sequence shown in FIG. 5 and which defines a gene promoter region has been isolated from maize roots. The promoter may be used for driving expression of foreign genes in the roots of plants. This is particularly useful for expressing an insecticidal toxin, such as a delta-endotoxin of *Bacillus thuringiensis*, to impart resistance to insect attack on the roots of plants by Coleopteran insects.

16 Claims, 13 Drawing Sheets

FIG. 1A

```
            ---------Vector-----------><EcoR1 >
         10         20         30         40         50         60
                                                              --- ---
  1  CGCCAAGCTT GGGCTGCAGG TCGACTCTAG AGGATCCCCG GGCGAGCTCG AATTCCTTTT
     GCGGTTCGAA CCCGACGTCC AGCTGAGATC TCCTAGGGGC CCGCTCGAGC TTAAGGAAAA 61  TTTTTTTTT TTTAATGATA ATTGGCATAT ATATATACAC GCTAACACGC TCGCGCGCTG
     AAAAAAAAAA AAATTACTAT TAACCGTATA TATATATGTG CGATTGTGCG AGCGCGCGAC 121  GGCAGAAACC AAAGCAATTA TTAACGCATC CAGGTAGCCC AGCCGAATTA CAACACGCAG
     CCGTCTTTGG TTTCGTTAAT AATTGCGTAG GTCCATCGGG TCGGCTTAAT GTTGTGCGTC 181  CTGCTCATAA TTCAACAAAC CCAAGTACAC AACATCCAGA CCGACCGTGA CTTTTGACTT
     GACGAGTATT AAGTTGTTTG GGTTCATGTG TTGTAGGTCT GGCTGGCACT GAAAACTGAA 241  GGGACCAAAA TAAAGCCCGT ACGTACCACG TCCTACACAA GCAGCAACAC TCACTGCCAG
     CCCTGGTTTT ATTTCGGGCA TGCATGGTGC AGGATGTGTT CGTCGTTGTG AGTGACGGTC 301  AGTCACGCGA TCCACCTTAA TAGAGCACAC GGACCTTGAC CAGGCGATCC ACCTTGAAAC
     TCAGTGCGCT AGGTGGAATT ATCTCGTGTG CCTGGAACTG GTCCGCTAGG TGGAACTTTG 361  AAACTTTTGG TAAAAGCAAA CAGAACCCAA CACACATGCC AACGCTAGCT AGCTTCTAAT
     TTTGAAAACC ATTTTCGTTT GTCTTGGGTT GTGTGTACGG TTGCGATCGA TCGAAGATTA
```

```
421  CCGCCGCCNA CGGCCAGGAC ACGCTGCGAC GCGACCTTAA TTAGAGGAGC TGGTCCTGTG
     GGCGGCGGNT GCCGGTCCTG TGCGACGCTG CGCTGGAATT AATCTCCTCG ACCAGGACAC

481  CTCGCNNNGN CCGCCTTGTG GTCTGCTTCC TCACCTGAGT CTTGTGGTAG CCGGCTATCT
     GAGCGNNNCN GGGGAACAC  CAGACGAAGG AGTGGACTCA GAACACCATC GGCCGATAGA

541  TGTCCATGAT CTTGCCCAGC AAACCCTTCT TCTCCCTTGCC ATCCGGGGCGC TCACGTTCTC
     ACAGGTACTA GAACGGGTCG TTTGGGAAGA AGAGGAACGG TAGGCCCGCG AGTGCAAGAG

601  GGCGTGCGGC GCTGGGCGCCG GGCGGTGGAC GCTTCTCCTT AGCAGGCCTT TCTTGGAATT
     CCGCACGCCG CGACCCGCCG CCGCCACCTG CGAAGAGGAA TCGTCCGGAA AGAACCTTAA

661  CTTGTTGTGG CCACCGGGGA GCTTCTCCCTT GATCTTGTCC AGCAGGCCTT TCTTGGAATT
     GAACAACACC GGTGGCCCCT CGAAGAGGAA CTAGAACAGG TCGTCCGGAA AGAACCTTAA

721  CACTGGGCCGT CGTTTTCAAC GTCGTGACTG GGAAAACC                    <EcoR1
     GTGACCGGGCA GCAAAAGTTG CAGCACTGAC CCTTTTGG

><------------Vector----------->
```

SEQ ID NO: 1
SEQUENCE TYPE: Nucleotide
SEQUENCE LENGTH: 1333 base pairs
STRANDEDNESS: Single
TOPOLOGY: Linear
MOLECULE TYPE: cDNA ORIGINAL SOURCE ORGANISM: Zea Mays
IMMEDIATE EXPERIMENTAL: Maize seedling root cDNA library

FEATURES:

PROPERTIES: cDNA of gene with enhanced root expression - pMR7/10.1

```
ACTGAAGCCA GTCAATAGCG AGTTCTAGAA CTAGTAGATA GCCTGCTGAT CTGTTCTGTT    60
GTTTAGTTCG CAAAGCCTTC TGTTTCGGCG ACCATGGAGG ATGAGAGGAA CACCCAGCAG   120
CACCAGGGCG GTGAGGCCNA GCAGGACGCT GCCGGTCAGG TGGAGGTGAA GGATAGGGGG   180
CTCCTGGACA GCCTTCTCGG CAGGAAGAAG CACGACGACG ACCAGGAGAA GAAGAAGCAG   240
ACGGAGGAGC TGGCGACCGG CATGGAGAAG GTCACGGTGT CCGAGCCCGA GAAGCACGGG   300
CACAAGGAGG AGGAGCACGA GGTCGTCGGC GAGAAGAAGG AGGGCCTTTT CGCCAAGCTG   360
```

FIG. 2B

```
CACCGCACCA GTTCCAGCTC CAGCTCGTCG AGCGACGAGG AAGAGGAGGC GATCGATGAG    420
AACGGCGAGA TTATCAAGAG GAAGAAGAAG AAGGTGGGCC TCAAGGAGAA GATCAAGGAG    480
AAGCTGCCGG GCGCACGAAG GACGGCCACC ACACGGCCGC ACCGTCCCCG GCGCCCGCGC    540
CCGCGCCCGT GGAGACGCAT GCCCACCACC AGGAGGAAGC GNATCACNGG CCGCACGTCG    600
TCCCGGCCCC GGCGCCTCCA CCGCACGTGG AGACGCACGT CCACCAGCAC GACCACGGCG    660
TCGTCGTCCA GAAGGTCGAG GACGACGTGA AGACCGAGAC CCCGCCGCAT GCACCGGGGG    720
AGGAGAAGAA AGGCCTGCTG GACAAGATCA AGGAGAAGCT CCCCGGTGGC CACAACAAGA    780
AGCCTGAAGC CGCTGCCGCA CCGGCTCCGC CCGTCCACGC GCCGGCGCCA GCGCCGCACG    840
CCGAGAACGT GAGCAGCCCG GATGGCAAGG AGAAGAAGGG TTTGCTGGGC AAGATCATGG    900
ACAAGATAGC CGGCTACCAC AAGAGCTCAG GTGAGGAAGC AGACCACAAG GCGGACGCCT    960
GCCGGGCGAGC ACAGGACCAG CTCCTCTAAT TAAGGTCGCA GTCGCAGCGT GTCCTGGCCG   1020
TGGGGGCGG ATTAGAAGCT AGCTAGCGTT GGCATGTGTG TTGGGTTCTG GTTTGCTTTT    1080
ACCAAAAGTT TGTTTCAAGG TGGATCGCCT GGTCAAGGTC CGTGTGCTCT ATTAAGGTGG   1140
```

FIG. 2C

```
ATCGCGTGAC TCTGGCAGTG AGTGTTGCTG CTTGTGTAGG ACGTGGTACG TACGGGCTTT    1200
ATTTTGGTCC CAAGTCAAAA GTCACGGTCG GTCTGGATGT TGTGTACTTG GGTTTGTTGA    1260
ATTATGAGCA GCTGCCGTGT GTAATTCGGC TGGGCTACCT GGATGCCGGTT AATAATTGCT   1320
TTGGTTTCTG CCC                                                       1333
```

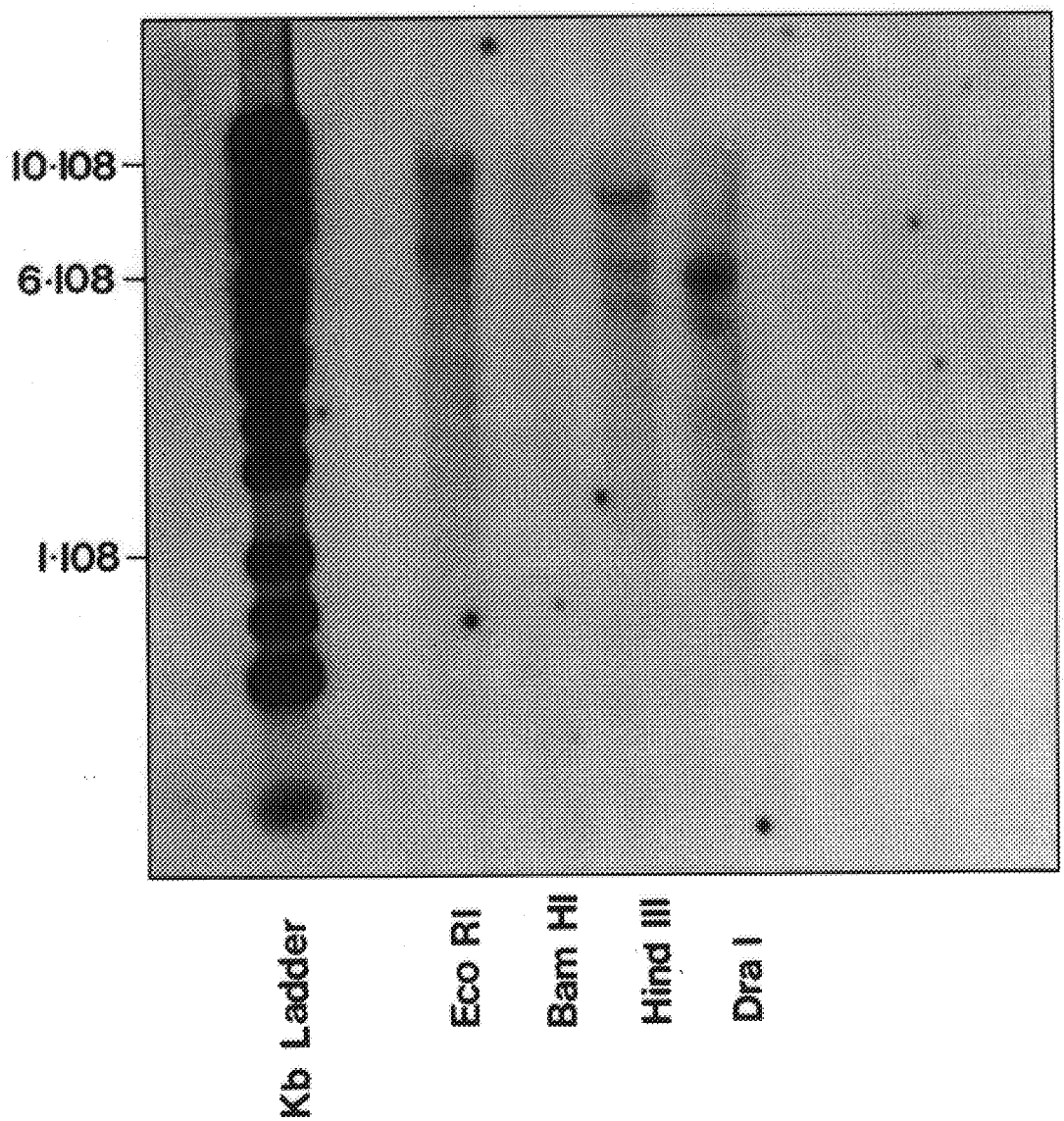

FIG. 5A

|  | 10 | 20 | 30 | 40 | 50 | 60 |
|---|---|---|---|---|---|---|
| 1 | CCATGGCTGC | ACACAATGTG | AGGACTCTCA | TCTACTCCAG | CACGTGTGTG | ACCTATGGAG |
| 61 | AGCCTGACAA | GATGCCCATC | GCTGAAGGAA | CTCCCCAGGT | CAGCAGTTCA | GGTCTGATTT |
| 121 | CTGAAACCAT | TAGTTCCTTT | CTAACATAGC | ATGTTCCTAG | GTTGCTTTCT | TATTTGTCTG |
| 181 | TGTTGTCTCC | CACATGTTCT | TATATCTGCA | TCTTTAGAAA | GCTTGGATAT | TGATGACATC |
| 241 | TATTATTAGG | TCCATGCTCT | CAGGCGTTGT | TTGGACGGTG | GCTAACAGGC | TCCCAAGCAA |
| 301 | ACCCACCTAG | GCTCATGTTT | ATTATCTATC | TCTTTTTGAA | AAGTTACACA | TTTACTTTGT |
| 361 | TGCCTGTGAG | CAGGGAATAC | GTTGGAGAA | AATGTATCAC | ATTTGGTGCC | AGGTTCAATT |
| 421 | TGGTTTCTGC | AAAGTTTATC | ACTCCTACAT | TTTCGCAATT | AGTTTCTACA | AAGTATATCA |
| 481 | CTCCATTCCA | CTCCTATGAA | ATTACTATGA | CTTAATTTCA | ATCGAGGTCA | TCTTCTTGCT |
| 541 | CCTTCGCTTG | CTTAGCAGTA | AGACATAACT | TCCTTTACCT | TGCTCAATAG | TTTGCCTTTT |
| 601 | AATTTGAACA | AAAATCTAAT | CACCTGACAT | TGCATGGGAG | GTAAGCTCCT | GTTTTCACA |
| 661 | AACTTTATCG | GTGGACAGAT | CACAGTCCTG | ACAGACCCAT | TAGTCCGATA | GAACAGTTAG |

FIG. 5B

```
 721  CATTAGGTAA ATATTTTGCC AATTGGCAAT TTTGATCTAC TCCTATTTTA AAATGCCATC
 781  ATAGGGGTGC TTGCATTTCT TGTTCATGAT TTTATTACTC AAGTCAAAAG TCTGCTTTTT
 841  ATATTACCTA TTACATATGC ATGGAAAAGC ATGTAGAAGG TAACACCAAT AAAGTTTGGA
 901  TCATATGTTT CCATCTATAA TGGTTGTCTT GGTATTCTCA ATCAGTGGAC TTGTGCAACT
 961  ATGTAATTTG CAGTCTCCAT AAGGATGCTA ATGATAGGTC CTCAACACAA GCCTTATTGG
1021  TAAGCTGAAA AACAACTTCA CACCTTCATT TCATTTCAAT AATCGTCTAC AAGACTAAAC
1081  CACTTATCTT ATCCTTCCCT TCCTGTTGTC TTTGATGCAG GACCATCCAT TCTTGAGCGT
1141  GTATGATGAC CTACATGTAG GACGGGATCT CCCCTCGCCA CCTTCAAGTA ATGACAGTGT
1201  ACTTGTTCTT CTTTTTATGT ATCCATCGTT TATCCTCCTT GTGCACATAA GTGATACATT
1261  TTATTTTACG TTTCAGGCAA CTCTAATATT TATCCTCCTT ATTAAGCAAA GAGTGTGGTG
1321  ACACATTTCC CTTTTGGGCA AGGGTTGGGT TGTGTACTGA GCTGTAATGA TTCGCAATTC
1381  ACCTGATATC ATGATTTAGA TGGTTTTCTG AAAGTGCATT GAGCCATTAG GAAACACAAG
1441  TGGGATGTAG TGATAACAAA TCTTTTTAGT CACAAAGATT TTTTTCTTG GAACCATTAA
```

FIG. 5C

```
1501  TAGTTGGCTA ACAGCTACAA TGATACAAGC GTTTGTTTTA ATATGTTGTG AATTGCAATG
1561  GTTACAATTG CCTTGTTTTG TTTGCAAACA GACTACCTTA TCTGGTTCTC AAGGTTCCTT
1621  CATGGCCTTG ACTCTCAAGA TCAGAGTATT CTTGTCAATG GGATATCAAT GAAGGTAAAG
1681  GTTCCACCC  CTATCTTTTC TCAACCTACC CATTTCTCT  AAAATACAAT AAAAAGCTTT
1741  TGAATTATTG AGTTTGGAAA CATGCAATTC ACAAAAAAAT GGAATTCTC  CTAAATTGAA
1801  GAATTTGTAA TCTTCTCTTG TAGGCTCGTT CGCCTTGTCA CAAGCTCCAT CGTTTAAGGA
1861  AAGAATATGC ATACACATTT GAAAGCACAA GCTTATCTTA TCAGTGTTCT GAGGTTACCA
1921  GGATCTTGCA AGGTAGCGCA CCATAGTAAT TGCAGCCATA ATGAAGACAG GCTGAGCTTA
1981  GATCAGAGCC CAGCAAGAAG GTATGGATCT TTACTTGTTG CTATTCTTGT CCATTTGGTT
2041  CAGGGGGTGG TTTATGAATA TTCAATCTGT TTATTACACC ATTCACAATT CGGCAGTATC
2101  GCATGGTTAA ATTCAGAAAT CAAAGATCTG ATATAATGGT GTATTGGAAT CATGAGTAGT
2161  TTGAGAAGAT TCCTGGTTAC ATGGAATGAA AGGCTGACTT ACACTTCAAG TTTCATCAAG
2221  TCATCACTAT TAGTGATGTC GTCCTCATTG ATGTCACTTG CTGTGTGCCT GTGCTCATGT
```

FIG. 5D

```
2281  TCTAGAATTT AATTACTGAT TACCATTGGT GGGCATTTTA TATGTAATAT GCTGCTCCTG
2341  TTTTCTGGAG GCAGGGGTGT TAAAGTAGTG TCATCAATTA TACAAAGTCA AATTTCTTGC
2401  AGGGAACCAT GTGATCTGTT GTGTTTAAAG CTTGTTTATT AGTTTTCTAT AAGCTGAACA
2461  AGTTCCTTCG CATTGTTTT GGATTGCAGA ATGAATACTT TTTCAAGTAC AGGGACGCCC
2521  GAAATGCAGC AGAAACTTTC AGAGCCAATG GAGATATAAA TAGACTTATA TCACACTGTA
2581  ATAGTCAGGT AAATCGCACA GCCTGTCTTC ATTATGGCTG CAATTACTAT ATCAGCATTT
2641  AATCTGGTTT GGTTTCTGTT GATTAAGCTG GTTTGATATT CCATATGCCT TTTGCTAATT
2701  AAGTAACGGT ACAAGTTCAT ACCATTAATG TTTGCAAGTG CTTCTGCTCA TTATATGTAT
2761  TCCAGTACTA CAACTAAGCA TTGTATCTGA AGTCCTACCC TTCGAATAAC TACCAGCGTT
2821  TTGGAGACTC CTACATTTTT TTGTCCATTG GACTGTTATT AAAGTTCAAC TCTCATGTGT
2881  ACTGGTTCTA AAATACAATG CTCTCTTGTC TCATCATTTT GTGACGTGCC AGCCAATATT
2941  TTTTCCTCT TTTAGATTGA GAGAGTTATG GAAATATGGA ACAAAAACGA GGACTTCCGC
3001  AAGCAGTATG TTGAATCGAA CAAGGTTAGC ACACTAAAGA GATTAGGGAC CCATGACGGA
```

FIG. 5E

```
3061  CGAAAACTTG GCCCTGGTGA GGATCCTCCG GTCATTCCAA GCCGAAGACC AAGCAACATT
3121  TATCCATTGT CTGCCCTCAAG CCCGGAAGTG ATCACCTTAG CTTCAACACC AGCACCTGTA
3181  TTGGCTGCTG CAGCTGCAGT CCCTTCCAAA GAGAACTCTT TTCCTGCTTT GGACGCCCCT
3241  CACATTGTTT CGATTCTCTG TGGTCTGTAC TTAATAAGTA GTCTATTTAT TTCGTGTGAT
3301  TGATCAGACA CCGTTCTCTG CATGCCAACA TCTAGCTGAT GAAGCACCCT CCTGAAGTTA
3361  TTTGATATTG TATACTGATA AGTAATAAAC TAGATTATGT AGTTCCTATA ATTTTATCA
3421  TATTGATTCC GTAGCAACGC ACGAGCATAT ACCTATAACA ATATAAGACA TATTTGTAT
3481  ATATAACACA TGTGCATATA TAAGTTATCG AGATATTATC GTCTCTCGTT GCAACGCACG
3541  TGCACTGACC TATAAAAGTA TAACACACAT TTGTACATAG TTTATCGTGG TTTTATACGT
3601  TTCGTTGCAA CGCACGGGCA CTCTCCTAGT ATATATTTAT TGATGGTTTC ATCTCTACCC
3661  GTATGTAAAT ATTCTTATAT TATTGTGAA TGATTCATCT CTAACCGTCT GTGAATGGTT
3721  TATATATATG CGTTATTCTT CACTAGGCAA AACAAAAACC ACGCCGACCG CCGACCGACC
3781  CGGCCTGTCC ACATGGCGCC GACCTCTCCC GACGCCGTCC ACCGCAGTGA TACCGCACCT
```

FIG. 5F

```
3841  CGACTCCTCG AGCATCGCCA CATGCCCACG TCCGATCCGG GCGCCCACG CGCGGGGTAC
3901  GACAGCGTCG TGGGCGACT  GGCCACCAGA CATGTCCCTCG TCGGCCAACC GACAGTCCGT
3961  TTCCGCCGCG GCTGATCTGT CCCCTCCTGC GTGCGTAGCC TACGCGTACA CGAAAACGAA
4021  CGTGACTTTC GGTGGCCTAG CTTGCTGATG CTCTATATAA GGACTGCCGG CCTCGATACC
4081  TCTCCATCCC TAAGCCAAAA GGCACTGAAAG AAGCCAGTCA ATAGCGAGTT CTAGAACTAG
4141  TAGCTAGCCT GCTGATCTGT TCTGTTGTTT AGTTCGCAAA GCCTTCTGTT TCGGCGACCA
4201  TGG

Total number of bases is: 4203

Sequence composition: 1119 A; 905 C; 799 G; 1380 T;
```

ROOT-SPECIFIC PROMOTER

This is a continuation-in-part of Ser. No. 08/111,590, filed Aug. 25, 1993, now abandoned, which is a continuation of Ser. No. 07/669,433, filed Mar. 15, 1991, now abandoned.

FIELD OF THE INVENTION

This invention relates to a gene promoter sequence which directs expression of a gene to the root tissue of plants.

BACKGROUND OF THE INVENTION

In the genetic improvement of plants by molecular techniques, it is desirable that expression of inserted foreign genes be restricted to tissue where that expression will have significant effect. There are two principal reasons for this. First, restricted expression, rather than total (constitutive) is likely to be less demanding on the metabolism of the plant. Secondly, it would be good practice to direct expression of the foreign gene to those parts of the plant which are not used for human or animal food when the expressed protein has no effect on such food parts. This second reason may be important when the effect which ingestion of the expressed protein may have is not fully known.

One widespread target for genetic improvement of crop plants is the introduction of resistance to insect attack. Certain insect species attack green leaf tissue, whereas others, for example Coleoptera, attack the roots. Similarly there are certain disease-inducing microorganisms which attack the below-ground plant tissue and any genetic modification to impart resistance to such organisms will require expression of the resistance-imparting gene in the roots.

SUMMARY OF THE INVENTION

An object of the present invention is to provide a root-specific gene promoter sequence and means for isolating same of root DNA.

According to the present invention there is provided a DNA sequence, defining a promoter of a root-expressed plant gene, having the sequence set forth in FIGS. 5A to 5F (SEQ ID NO:3) herewith.

The said DNA may be isolated from the root tissue of a particular target plant species of interest. The preferred species is *Zea mays*.

The invention also provides a gene construct comprising, in sequence, the aforesaid gene promoter of the invention, a coding region located downstream and controlled by the said promoter and 3'-untranslated region including a polyadenylation signal.

Preferably the coding region encodes a protein which is toxic to root-attacking organisms and more preferably the protein is an insecticidal endotoxin of *Bacillus thuringiensis*.

Further according to the invention there is provided a plant genome into which the gene construct of the invention has been inserted by transformation.

BRIEF DESCRIPTION OF THE DRAWINGS

FIGS. 1A–B show a cDNA sequence which may be used to derive promoters according to the present invention.

FIGS. 2A–C show a cDNA sequence which may be used to derive promoters according to the present invention.

FIG. 3 shows the autoradiograph of a Northern blot probed with pMR7.

FIGS. 5A–F show a DNA sequence which defines a promoter of a root-expressed plant gene.

DETAILED DESCRIPTION OF THE INVENTION

Figure 4:
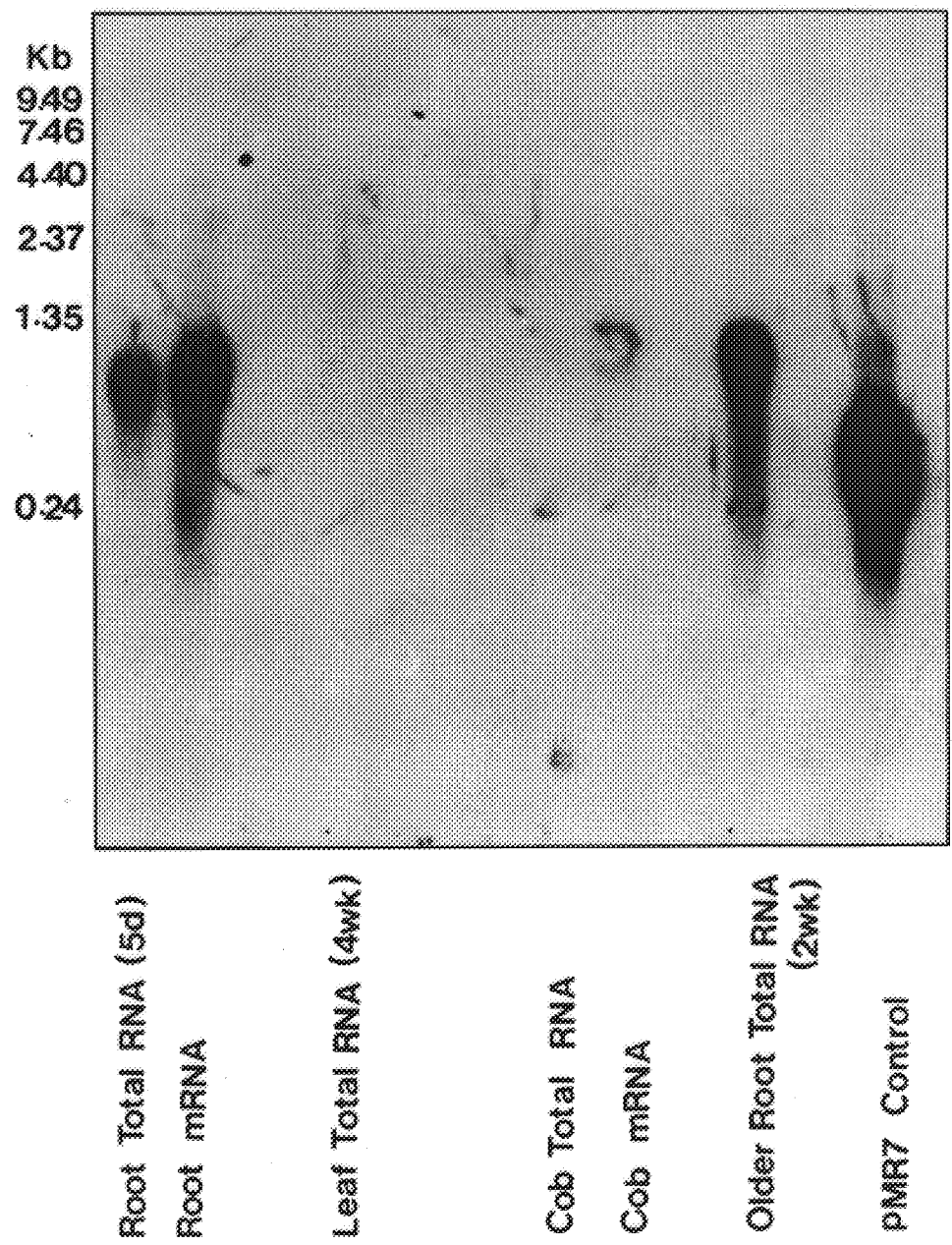
FIG. 4 shows the autoradiograph of a Northern blot probed with pMR12 which was typical of those clones which do not show root enhanced expression.

The promoter sequence of the invention may be isolated from the genomic sequence to which a cDNA derived from a root-expressed gene hybridises. A genomic library is screened using the said cDNA as a probe. Those genomic fragments which hybridise to the cDNA probe carry not only the structural gene but the promoter sequence associated therewith. The promoter may then be isolated by cleavage of the sequence around the location of the translation start point of the structural gene sequence. The sequences of suitable such cDNAs are shown in FIGS. 1A–B (SEQ ID NO:2) and 2A–C (SEQ ID NO:1) were isolated from maize.

These cDNAs have been deposited (1) in a plasmid designated pMR7 in an *E.coli* DH5α host and (2) in a plasmid designated pMR7/10.1 in an *E.coli* DH5α host, at the National Collection of Industrial and Marine Bacteria, Aberdeen, United Kingdom, on 15th Mar., 1990, under the Accession Number 40267. These deposits were made under the terms of the Budapest Treaty on the deposit of microorganisms for patent purposes.

Many genes specifying insecticidal proteins, particularly delta-endotoxin genes of *Bacillus thuringiensis* have been reported in the literature.

The invention will now be described, by way of illustration, by the following Examples.

EXAMPLE 1

Total RNA was extracted from root tissue of five-day old and fourteen-day old maize plants. For use in certain comparative tests which will be described later, total RNA was also isolated from maize leaf and immature cob.

The RNA samples were purified using the guanidinium thiocyanate/caesium chloride method and poly(a)+mRNA purified on an oligo(dT) column. The corresponding cDNAs were synthesised using the oligo dT priming method and the cDNA cloned into plasmid pUC13 after Tinkering.

The success of each of these stages was monitored by incorporation of a label. Digests of randomly picked clones from the cDNA library showed a size distribution for inserts of between 300 and 1300 base pairs.

Recombinants were individually transferred to microtitre wells, in total the library consisted of about 7,000 clones.

Clones representing genes with root enhanced expression were identified by differential screening. Identical filters were prepared from the microtitre plates and hybridised separately with probes prepared by first strand synthesis of root mRNA and four week old leaf mRNA. The autoradiographs were superimposed and recombinants showing root enhanced expression were selected as showing a more intense signal with the root probe than with the leaf probe. Interestingly, none of the selected clones showing differential hybridisation fell into the highly expressed category; all examples of this type showed equally intense signals to both probes.

By this procedure, 235 clones were selected as potentially showing a degree of differential hybridisation after the first screen. This number was reduced to thirteen after further screens.

The cDNA inserts of these thirteen clones ranged from 300 to 1100 base pairs as judged by restriction digestion or PCR. The inserts of each of the thirteen candidate inserts were then used in Northern hybridisations to confirm their tissue specificity.

RNAs from the five-day and fourteen day old root tissue and, for comparison, from leaf and cob tissue were probed to identify any which were expressed in root tissue but not in leaf or cob.

By these procedures, the clone designated pMR7 showed enhanced expression in both the five and the fourteen day old root and only insignificant expression in leaf and cob.

FIG. 3 herewith shows the autoradiograph of a Northern blot probed with pMR7. For comparison purposes, FIG. 4 shows the auto- radiograph of a Northern blot probed with pMR12 which was typical of those clones which do not show root enhanced expression. Comparison of FIGS. 3 and 4 shows that whereas pMR7 hybridised to both five- and fourteen-day old root RNA with little hybridisation to either leaf or cob RNA, pMR2 gave strong signals on five-day old root RNA, much reduced signal on fourteen day old root but strong signals to both leaf and cob RNA.

Thus pMR7 has been selected for further analysis. The insert of pMR7 is 700 base pairs in length and has been fully sequenced by walking through its length by synthesising oligonucleotides at approximately 200 base pair intervals and performing direct plasmid sequencing. There is a poly (A)+tail. The sequence of the pMR7 insert is given in FIGS. 1A and 1B herewith.

Maize genomic DNA digests have been probed using pMR7 as a probe. Southern blots have indicated that the corresponding gene is of low copy number, that is, only a small number of hybridising bands are detectable at the level of stringency used.

From the screen of a partial Mbo1 genomic library a number of putative positives have been identified and from these the upstream promoter sequence which directs expression to root tissue can be isolated and sequenced.

The pMR7 insert was used to screen a second maize seedling root cDNA library constructed in the cloning vector lZAP II. From a number of positively hybridising clones, one, pMR7/10.1, was selected for further analysis. DNA sequencing indicated that pMR7/10.1 was completely homologous with pMR7 but was of longer length, perhaps representing the full length cDNA clone. The sequence of pMR7/10.1 is given in FIGS. 2A to 2C (SEQ ID NO:1) herewith.

EXAMPLE 2

A 'gene-specific' probe, representing the entire 3' untranslated region of the MR7 gene, was radioactively labelled and used to screen a commercial corn genomic library obtained from Clontech, USA (line W22). The probe, obtained by PCR using the cDNA as a template, was 350 bp in length and of lower G+C content than the entire cDNA, thereby reducing the chances of non-specific hybridisation.

Five clones were selected for further analysis after three rounds of plaque purification. Each hybridised strongly to oligonucleotide probes designed throughout the length of the pMR7 cDNA, confirming that they were closely related to the original cDNA. Restriction analysis of purified DNA obtained from these lambda clones indicated that 4 of them (numbers 7, 11, 14 and 15) were clearly related on the basis of similarity of restriction profiles. The other clone, number 10 had a different profile. Hybridisation of the MR7 gene-specific probe confirmed this relationship. Single or few hybridisation bands resulted from probing digests of each of the 5 lambda isolates, number 10 having a different profile than the other four.

Of the four more closely related lambda clones, number 7 was chosen for further analysis on the basis of its larger insert size of approximately 16 kb, estimated from restriction analysis (the other inserts ranging in size from 9.0 to 13.5 kb).

In order to identify a genomic fragment containing the MR7 promoter, the insert from lambda clone 7 was subcloned into pUC18 vectors. pMRP1 represents a 10 kb EcoRI fragment subcloned from lambda clone number 7. Partial sequencing with an internal primer confirmed that this fragment contained DNA related to that of pMR7/10.1 cDNA, as opposed to any related but distinguishably different classes of the MR7 gene.

Utilising restriction sites identified at the 5' end of the pMR7 cDNA, the upstream region of the MR7 gene contained within lambda clone 7 was identified and subsequently isolated on the basis of hybridisation to specific oligonucleotide probes designed against sequence in the cDNA upstream of the aforementioned sites. A 4.2 kb NcoI fragment was subcloned into pUC18 (pMRP2) which represents the region of the gene immediatly upstream of the ATG translation startpoint (the ATG being a part of the 3' NcoI restriction site).

From within the insert of pMRP2, a 1.9 kb XbaI fragment was also identified which represented a region expected to contain an active gene promoter.

The entire 4.2 kb region of pMRP2 was sequenced. The sequence is given in FIG. 5A to 5F (SEQ ID NO:3) herewith. Short sequences sharing homology with a number of promoter 'sequence motifs' described in the literature can be recognised.

The technique of primer extension was utilised to identify the transcription start point within the promoter region. A possible transcription start point was identified 25 nucleotides downstream of the A+T region thought to represent the 'TATA' box of the MR7 promoter.

To confirm the activity of the putative promoter regions, both the 4.2 kb NcoI fragment and the 1.9 kb XbaI fragment were cloned into a 'promoter assay construct', in which they were fused to a the easily assayable B-glucuronidase (GUS) gene. In the former case (pMRP3), there was precise fusion through the ATG of the NcoI site. In the latter case (pMRP4), the fusion was a transcriptional one, the resulting expression construct also containing the 'enhancing' maize AdhI Intron I sequence within the transcribed region.

Plasmid DNA of both pMRP3 and pMRP4 were used in transient expression experiments in maize protoplasts derived from several sources, including root, leaf and endosperm tissue. In each case, expression of GUS from the constructs was classifed as 'high', being greater than control plasmids in which GUS expression was driven by 'standard' promoters such as 35S and maize Adh. High level GUS expression from these two constructs was also demonstrated by bombardment of root, leaf and coleoptile tissues of maize seedlings.

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 1333 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

```
ACTGAAGCCA  GTCAATAGCG  AGTTCTAGAA  CTAGTAGATA  GCCTGCTGAT  CTGTTCTGTT      60
GTTTAGTTCG  CAAAGCCTTC  TGTTTCGGCG  ACCATGGAGG  ATGAGAGGAA  CACCCAGCAG     120
CACCAGGGCG  GTGAGGCCNA  GCAGGACGCT  GCCGGTCAGG  TGGAGGTGAA  GGATAGGGGG     180
CTCCTGGACA  GCCTTCTCGG  CAGGAAGAAG  CACGACGACG  ACCAGGAGAA  GAAGAAGCAG     240
ACGGAGGAGC  TGGCGACCGG  CATGGAGAAG  GTCACGGTGT  CCGAGCCCGA  GAAGCACGGG     300
CACAAGGAGG  AGGAGCACGA  GGTCGTCGGC  GAGAAGAAGG  AGGGCCTTTT  CGCCAAGCTG     360
CACCGCACCA  GTTCCAGCTC  CAGCTCGTCG  AGCGACGAGG  AAGAGGAGGC  GATCGATGAG     420
AACGGCGAGA  TTATCAAGAG  GAAGAAGAAG  AAGGTGGGCC  TCAAGGAGAA  GATCAAGGAG     480
AAGCTGCCGG  GCGCACGAAG  GACGGCCACC  ACACGGCCGC  ACCGTCCCCG  GCGCCCGCGC     540
CCGCGCCCGT  GGAGACGCAT  GCCCACCACC  AGGAGGAAGC  GNATCACNGG  CCGCACGTCG     600
TCCCGGCCCC  GGCGCCTCCA  CCGCACGTGG  AGACGCACGT  CCACCAGCAC  GACCACGGCG     660
TCGTCGTCCA  GAAGGTCGAG  GACGACGTGA  AGACCGAGAC  CCCGCCGCAT  GCACCGGGGG     720
AGGAGAAGAA  AGGCCTGCTG  GACAAGATCA  GGAGAAGCT   CCCCGGTGGC  CACAACAAGA     780
AGCCTGAAGC  CGCTGCCGCA  CCGGCTCCGC  CCGTCCACGC  GCCGGCGCCA  GCGCCGCACG     840
CCGAGAACGT  GAGCAGCCCG  GATGGCAAGG  AGAAGAAGGG  TTTGCTGGGC  AAGATCATGG     900
ACAAGATAGC  CGGCTACCAC  AAGAGCTCAG  GTGAGGAAGC  AGACCACAAG  GCGGACGCCT     960
GCCGGCGAGC  ACAGGACCAG  CTCCTCTAAT  TAAGGTCGCA  GTCGCAGCGT  GTCCTGGCCG    1020
TGGGCGGCGG  ATTAGAAGCT  AGCTAGCGTT  GGCATGTGTG  TTGGGTTCTG  GTTTGCTTTT    1080
ACCAAAAGTT  TGTTTCAAGG  TGGATCGCCT  GGTCAAGGTC  CGTGTGCTCT  ATTAAGGTGG    1140
ATCGCGTGAC  TCTGGCAGTG  AGTGTTGCTG  CTTGTGTAGG  ACGTGGTACG  TACGGGCTTT    1200
ATTTTGGTCC  CAAGTCAAAA  GTCACGGTCG  GTCTGGATGT  TGTGTACTTG  GGTTTGTTGA    1260
ATTATGAGCA  GCTGCGTGTT  GTAATTCGGC  TGGGCTACCT  GGATGCGGTT  AATAATTGCT    1320
TTGGTTTCTG  CCC                                                           1333
```

( 2 ) INFORMATION FOR SEQ ID NO:2:

( i ) SEQUENCE CHARACTERISTICS:
        ( A ) LENGTH: 758 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:2:

```
CGCCAAGCTT  GGGCTGCAGG  TCGACTCTAG  AGGATCCCCG  GGCGAGCTCG  AATTCCTTTT      60
```

```
TTTTTTTTTT   TTTAATGATA   ATTGGCATAT   ATATATACAC   GCTAACACGC   TCGCGCGCTG      120

GGCAGAAACC   AAAGCAATTA   TTAACGCATC   CAGGTAGCCC   AGCCGAATTA   CAACACGCAG      180

CTGCTCATAA   TTCAACAAAC   CCAAGTACAC   AACATCCAGA   CCGACCGTGA   CTTTTGACTT      240

GGGACCAAAA   TAAAGCCCGT   ACGTACCACG   TCCTACACAA   GCAGCAACAC   TCACTGCCAG      300

AGTCACGCGA   TCCACCTTAA   TAGAGCACAC   GGACCTTGAC   CAGGCGATCC   ACCTTGAAAC      360

AAACTTTTGG   TAAAAGCAAA   CAGAACCCAA   CACACATGCC   AACGCTAGCT   AGCTTCTAAT      420

CCGCCGCCNA   CGGCCAGGAC   ACGCTGCGAC   GCGACCTTAA   TTAGAGGAGC   TGGTCCTGTG      480

CTCGCNNNGN   CCGCCTTGTG   GTCTGCTTCC   TCACCTGAGT   CTTGTGGTAG   CCGGCTATCT      540

TGTCCATGAT   CTTGCCCAGC   AAACCCTTCT   TCTCCTTGCC   ATCCGGGCGC   TCACGTTCTC      600

GGCGTGCGGC   GCTGGCGCCG   GCGCGTGGAC   GGCGGAGCGG   TGCGGCAGCG   GCTTCAGCTT      660

CTTGTTGTGG   CCACCGGGGA   GCTTCTCCTT   GATCTTGTCC   AGCAGGCCTT   TCTTGGAATT      720

CACTGGCCGT   CGTTTTCAAC   GTCGTGACTG   GGAAAACC                                 758
```

(2) INFORMATION FOR SEQ ID NO:3:

(i) SEQUENCE CHARACTERISTICS:
        (A) LENGTH: 4203 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
CCATGGCTGC   ACACAATGTG   AGGACTCTCA   TCTACTCCAG   CACGTGTGTG   ACCTATGGAG       60

AGCCTGACAA   GATGCCCATC   GCTGAAGGAA   CTCCCCAGGT   CAGCAGTTCA   GGTCTGATTT      120

CTGAAACCAT   TAGTTCCTTT   CTAACATAGC   ATGTTCCTAG   GTTGCTTTCT   TATTTGTCTG      180

TGTTGTCTCC   CACATGTTCT   TATATCTGCA   TCTTTAGAAA   GCTTGGATAT   TGATGACATC      240

TATTATTAGG   TCCATGCTCT   CAGGCGTTGT   TTGGACGGTG   GCTAACAGGC   TCCCAAGCAA      300

ACCCACCTAG   GCTCATGTTT   ATTATCTATC   TCTTTTGAA    AAGTTACACA   TTTACTTTGT      360

TGCCTGTGAG   CAGGGAATAC   GTTGGAGAA   AATGTATCAC   ATTTGGTGCC   AGGTTCAATT       420

TGGTTTCTGC   AAAGTTTATC   ACTCCTACAT   TTTCGCAATT   AGTTTCTACA   AAGTATATCA      480

CTCCATTCCA   CTCCTATGAA   ATTACTATGA   CTTAATTTCA   ATCGAGGTCA   TCTTCTTGCT      540

CCTTCGCTTG   CTTAGCAGTA   AGACATAACT   TCCTTTACCT   TGCTCAATAG   TTTGCCTTTT      600

AATTTGAACA   AAAATCTAAT   CACCTGACAT   TGCATGGGAG   GTAAGCTCCT   GTTTTTCACA      660

AACTTTATCG   GTGGACAGAT   CACAGTCCTG   ACAGACCCAT   TAGTCCGATA   GAACAGTTAG      720

CATTAGGTAA   ATATTTTGCC   AATTGGCAAT   TTTGATCTAC   TCCTATTTTA   AAATGCCATC      780

ATAGGGGTGC   TTGCATTTCT   TGTTCATGAT   TTTATTACTC   AAGTCAAAAG   TCTGCTTTTT      840

ATATTACCTA   TTACATATGC   ATGGAAAAGC   ATGTAGAAGG   TAACACCAAT   AAAGTTTGGA      900

TCATATGTTT   CCATCTATAA   TGGTTGTCTT   GGTATTCTCA   ATCAGTGGAC   TTGTGCAACT      960

ATGTAATTTG   CAGTCTCCAT   AAGGATGCTA   ATGATAGGTC   CTCAACACAA   GCCTTATTGG     1020

TAAGCTGAAA   AACAACTTCA   CACCTTCATT   TCATTTCAAT   AATCGTCTAC   AAGACTAAAC     1080

CACTTATCTT   ATCCTTCCCT   TCCTGTTGTC   TTTGATGCAG   GACCATCCAT   TCTTGAGCGT     1140

GTATGATGAC   CTACATGTAG   GACGGGATCT   CCCCTCGCCA   CCTTCAAGTA   ATGACAGTGT     1200

ACTTGTTCTT   TTAATCTTTT   CTTTTTATGT   ATCCATCGTT   GTGCACATAA   GTGATACATT     1260
```

| | | | | | | |
|---|---|---|---|---|---|---|
| TTATTTTACG | TTTCAGGCAA | CTCTAATATT | TATCCTCCTT | ATTAAGCAAA | GAGTGTGGTG | 1320 |
| ACACATTTCC | CTTTTGGGCA | AGGGTTGGGT | TGTGTACTGA | GCTGTAATGA | TTCGCAATTC | 1380 |
| ACCTGATATC | ATGATTTAGA | TGGTTTTCTG | AAAGTGCATT | GAGCCATTAG | GAAACACAAG | 1440 |
| TGGGATGTAG | TGATAACAAA | TCTTTTTAGT | CACAAAGATT | TTTTTCTTG | GAACCATTAA | 1500 |
| TAGTTGGCTA | ACAGCTACAA | TGATACAAGC | GTTTGTTTTA | ATATGTTGTG | AATTGCAATG | 1560 |
| GTTACAATTG | CCTTGTTTTG | TTTGCAAACA | GACTACCTTA | TCTGGTTCTC | AAGGTTCCTT | 1620 |
| CATGGCCTTG | ACTCTCAAGA | TCAGAGTATT | CTTGTCAATG | GGATATCAAT | GAAGGTAAAG | 1680 |
| GTTTCCACCC | CTATCTTTTC | TCAACCTACC | CATTTTCTCT | AAAATACAAT | AAAAAGCTTT | 1740 |
| TGAATTATTG | AGTTTGGAAA | CATGCAATTC | ACAAAAAAT | GGAATTTCTC | CTAAATTGAA | 1800 |
| GAATTTGTAA | TCTTCTCTTG | TAGGCTCGTT | CGCCTTGTCA | CAAGCTCCAT | CGTTTAAGGA | 1860 |
| AAGAATATGC | ATACACATTT | GAAAGCACAA | GCTTATCTTA | TCAGTGTTCT | GAGGTTACCA | 1920 |
| GGATCTTGCA | AGGTAGCGCA | CCATAGTAAT | TGCAGCCATA | ATGAAGACAG | GCTGAGCTTA | 1980 |
| GATCAGAGCC | CAGCAAGAAG | GTATGGATCT | TTACTTGTTG | CTATTCTTGT | CCATTGGTT | 2040 |
| CAGGGGGTGG | TTTATGAATA | TTCAATCTGT | TTATTACACC | ATTCACAATT | CGGCAGTATC | 2100 |
| GCATGGTTAA | ATTCAGAAAT | CAAAGATCTG | ATATAATGGT | GTATTGGAAT | CATGAGTAGT | 2160 |
| TTGAGAAGAT | TCCTGGTTAC | ATGGAATGAA | AGGCTGACTT | ACACTTCAAG | TTTCATCAAG | 2220 |
| TCATCACTAT | TAGTGATGTC | GTCCTCATTG | ATGTCACTTG | CTGTGTGCCT | GTGCTCATGT | 2280 |
| TCTAGAATTT | AATTACTGAT | TACCATTGGT | GGGCATTTTA | TATGTAATAT | GCTGCTCCTG | 2340 |
| TTTTCTGGAG | GCAGGGGTGT | TAAAGTAGTG | TCATCAATTA | TACAAAGTCA | AATTTCTTGC | 2400 |
| AGGGAACCAT | GTGATCTGTT | GTGTTTAAAG | CTTGTTTATT | AGTTTTCTAT | AAGCTGAACA | 2460 |
| AGTTCCTTCG | CATTTGTTTT | GGATTGCAGA | ATGAATACTT | TTTCAAGTAC | AGGGACGCCC | 2520 |
| GAAATGCAGC | AGAAACTTTC | AGAGCCAATG | GAGATATAAA | TAGACTTATA | TCACACTGTA | 2580 |
| ATAGTCAGGT | AAATCGCACA | GCCTGTCTTC | ATTATGGCTG | CAATTACTAT | ATCAGCATTT | 2640 |
| AATCTGGTTT | GGTTTCTGTT | GATTAAGCTG | GTTTGATATT | CCATATGCCT | TTTGCTAATT | 2700 |
| AAGTAACGGT | ACAAGTTCAT | ACCATTAATG | TTTGCAAGTG | CTTCTGCTCA | TTATATGTAT | 2760 |
| TCCAGTACTA | CAACTAAGCA | TTGTATCTGA | AGTCCTACCC | TTCGAATAAC | TACCAGCGTT | 2820 |
| TTGGAGACTC | CTACATTTTT | TTGTCCATTG | GACTGTTATT | AAAGTTCAAC | TCTCATGTGT | 2880 |
| ACTGGTTCTA | AAATACAATG | CTCTCTTGTC | TCATCATTTT | GTGACGTGCC | AGCCAATATT | 2940 |
| TTTTTCCTCT | TTTAGATTGA | GAGAGTTATG | GAAATATGGA | ACAAAAACGA | GGACTTCCGC | 3000 |
| AAGCAGTATG | TTGAATCGAA | CAAGGTTAGC | ACACTAAAGA | GATTAGGGAC | CCATGACGGA | 3060 |
| CGAAAACTTG | GCCCTGGTGA | GGATCCTCCG | GTCATTCCAA | GCCGAAGACC | AAGCAACATT | 3120 |
| TATCCATTGT | CTGCCTCAAG | CCCGGAAGTG | ATCACCTTAG | CTTCAACACC | AGCACCTGTA | 3180 |
| TTGGCTGCTG | CAGCTGCAGT | CCCTTCCAAA | GAGAACTCTT | TTCCTGCTTT | GGACGCCCCT | 3240 |
| CACATTGTTT | CGATTCTCTG | TGGTCTGTAC | TTAATAAGTA | GTCTATTTAT | TTCGTGTGAT | 3300 |
| TGATCAGACA | CCGTTCTCTG | CATGCCAACA | TCTAGCTGAT | GAAGCACCCT | CCTGAAGTTA | 3360 |
| TTTGATATTG | TATACTGATA | AGTAATAAAC | TAGATTATGT | AGTTCCTATA | ATTTTTATCA | 3420 |
| TATTGATTCC | GTAGCAACGC | ACGAGCATAT | ACCTATAACA | ATATAAGACA | TATTTGTAT | 3480 |
| ATATAACACA | TGTGCATATA | TAAGTTATCG | AGATATTATC | GTCTCTCGTT | GCAACGCACG | 3540 |
| TGCACTGACC | TATAAAAGTA | TAACACACAT | TTGTACATAG | TTTATCGTGG | TTTTATACGT | 3600 |
| TTCGTTGCAA | CGCACGGGCA | CTCTCCTAGT | ATATATTTAT | TGATGGTTTC | ATCTCTACCC | 3660 |

-continued

| | | | | | | |
|---|---|---|---|---|---|---|
| GTATGTAAAT | ATTCTTATAT | TATTTGTGAA | TGATTCATCT | CTAACCGTCT | GTGAATGGTT | 3720 |
| TATATATATG | CGTTATTCTT | CACTAGGCAA | AACAAAAACC | ACGCCGACCG | CCGACCGACC | 3780 |
| CGGCCTGTCC | ACATGGCGCC | GACCTCTCCC | GACGCCGTCC | ACCGCAGTGA | TACCGCACCT | 3840 |
| CGACTCCTCG | AGCATCGCCA | CATGCCCACG | TCCGATCCGG | GCGCCCACG | CGCGGGGTAC | 3900 |
| GACAGCGTCG | TGGCGCGACT | GGCCACCAGA | CATGTCCTCG | TCGGCCAACC | GACAGTCCGT | 3960 |
| TTCCGCCGCG | GCTGATCTGT | CCCCTCCTGC | GTGCGTAGCC | TACGCGTACA | CGAAAACGAA | 4020 |
| CGTGACTTTC | GGTGGCCTAG | CTTGCTGATG | CTCTATATAA | GGACTGCCGG | CCTCGATACC | 4080 |
| TCTCCATCCC | TAAGCCAAAA | GGCACTGAAG | AAGCCAGTCA | ATAGCGAGTT | CTAGAACTAG | 4140 |
| TAGCTAGCCT | GCTGATCTGT | TCTGTTGTTT | AGTTCGCAAA | GCCTTCTGTT | TCGGCGACCA | 4200 |
| TGG | | | | | | 4203 |

We claim:

1. An isolated DNA sequence which codes for a promoter of a root-expressed plant gene, said gene having the sequence of FIGS. 5A–F (SEQ ID NO:3).

2. The isolated DNA sequence of claim 1 wherein said promoter has the sequence of a 1.9 Kb XbaI fragment of the sequence of FIGS. 5A–F (SEQ ID NO:3).

3. The isolated DNA sequence of claim 1 wherein said sequence is isolated from the root tissue of a target plant species.

4. The isolated DNA sequence of claim 3, wherein the target plant species is *Zea mays*.

5. An isolated DNA construct comprising, in sequence, the DNA sequence of claim 1 which comprises a promoter, a coding region located downstream and controlled by said promoter and a 3'-untranslated region including a polyadenylation signal.

6. An isolated DNA construct comprising, in sequence, the DNA sequence of claim 2 which comprises a promoter, a coding region located downstream and controlled by said promoter and a 3'-untranslated region including a polyadenylation signal.

7. The construct of claim 5, wherein the coding region encodes a protein which is toxic to root-attacking organisms.

8. The construct of claim 6, wherein the coding region encodes a protein which is toxic to root-attacking organisms.

9. The construct of claim 7, wherein the protein is an insecticidal endotoxin of *Bacillus thuringiensis*.

10. The construct of claim 8, wherein the protein is an insecticidal endotoxin of *Bacillus thuringiensis*.

11. A plant genome into which the construct of claim 5, has been inserted such that said promoter is transcriptionally active.

12. A plant genome into which the construct of claim 6 has been inserted such that said promoter is transcriptionally active.

13. A plant genome into which the construct of claim 7 has been inserted such that said promoter is transcriptionally active.

14. A plant genome into which the construct of claim 8 has been inserted such that said promoter is transcriptionally active.

15. A plant genome into which the construct of claim 9 has been inserted such that said promoter is transcriptionally active.

16. A plant genome into which the construct of claim 10 has been inserted such that said promoter is transcriptionally active.

* * * * *

UNITED STATES PATENT AND TRADEMARK OFFICE
CERTIFICATE OF CORRECTION

PATENT NO.     : 5,837,848
DATED          : November 17, 1998
INVENTOR(S)    : Ely et al.

It is certified that error appears in the above-identified patent and that said Letters Patent is hereby corrected as shown below:

<u>Column 2,</u>
Line 18, after "host" insert -- at the National Collection of Industrial and Marine Bacteria, Aberdeen, United Kingdom on March 12, 1991 under Accession Number 40380, --.

Signed and Sealed this

Fifth Day of August, 2003

JAMES E. ROGAN
*Director of the United States Patent and Trademark Office*